June 14, 1949. W. B. CLARKE Plant Pat. 847
FLOWERING QUINCE PLANT
Filed July 3, 1947
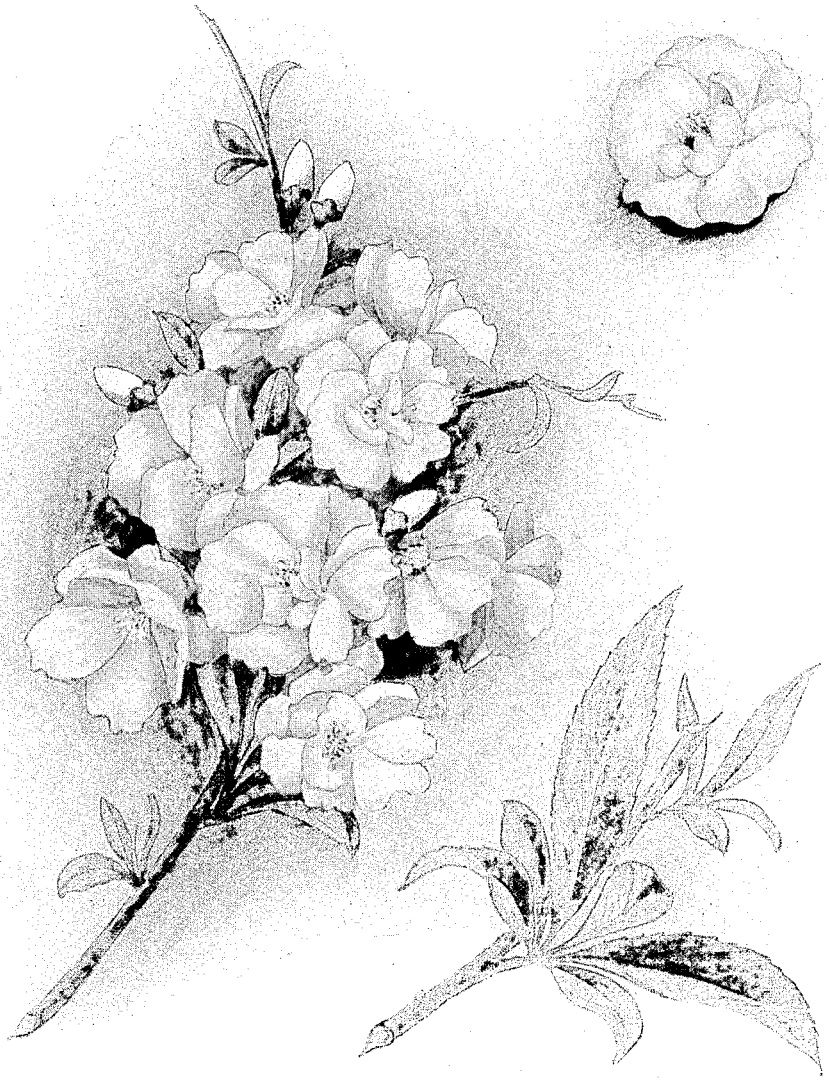
WITNESS
Addison E. Avery
INVENTOR
WALTER BOSWORTH CLARKE,
by Rummler Rummler & Snow,
ATTYS.

Patented June 14, 1949

Plant Pat. 847

UNITED STATES PATENT OFFICE

847

FLOWERING QUINCE PLANT

Walter Bosworth Clarke, San Jose, Calif., assignor to W. B. Clarke & Co., a partnership composed of Walter B. Clarke, James F. Clarke, and Walter C. Borchers, all of San Jose, Calif.

Application July 3, 1947, Serial No. 758,772

1 Claim. (Cl. 47—60)

The present invention relates to a new and distinct variety of flowering quince shrub, originating as a chance seedling in my breeding department at San Jose, California, which I found to have important characteristics distinguishing it from other known commercial varieties. The seed parent was "Mt. Everest Quince" which was also propagated on our breeding grounds and which in turn was a seedling of "Candida" that is about the best of the older single-flowered pure white quinces. This new variety of *Chaenomeles lagenaria*, Koidzumi, has been asexually reproduced by grafting and its novel features appear to be permanently fixed.

The unusual qualities of this new variety reside in its vigorous, healthy, erect and bushy habit of growth, large blooms which appear in the earliest part of the season as single-petaled, with the later ones, nearly all, double-petaled. Its unopened buds are lightly tipped with lavender coloring, while the flowers open pure white but are soon flushed with pink, giving them an "apple blossom" effect. When fully matured, and before falling, the flowers are completely of a soft shade of rose color, which is one of the most distinguishing characteristics of this new variety of quince and makes it outstanding different from other known varieties.

Another peculiarity of this new variety of flowering quince is the narrow structure of its long lanceolate leaves which is unusual for any kind of flowering quince.

Other features of novelty will appear more particularly in the following detailed description of the new quince:

Parentage: Seedling.
*Seed parent.*—Mt. Everest Quince.
*Pollen parent.*—Unknown.
Classification: Variety of *Chaenomeles lagenaria*, Koidzumi.

*Flower*

Blooming habit: Continuous while in bloom in the spring.
*Blooms.*—Midseason.
Bud: Usual size.
*Form.*—Pointed.
*Color.*—When petals begin to unfurl, white, with lavender tips.
Peduncle: Almost sessile.
Flower: *Size.*—2 inches in diameter.
*Borne.*—In cluster.
*Shape.*—When first open—flat.

*Petalage.*—*Number*—5 in earliest blooms, about 15 in later flowers. *Form*—rounded and slightly serrated. *Color*—when first open, pure white, soon flushed pink and becomes a soft rose shade when old. *Appearance*—satiny. *Persistence* — wither and fall off. *Lasting quality*—on plant, good; as cut flower, very good, particularly if cut when in bud.
Genital organs:
*Stamens.*—Usual length. Number about 20.
*Pollen.*—Color—yellow.
*Styles.*—Number 5.
*Ovaries.*—5 celled.
Fruit:
*Fertile.*—Yes.
*Shape.*—Elongated.
*Color at maturity.*—Yellow.

*Plant*

Form: Bushy.
*Height.*—At maturity approximately 7 or 8 feet.
*Growth.*—Vigorous. Branching—yes.
Leaves: *Texture.*—Slightly leathery and glossy.
*Shape.*—Long lanceolate, sharply serrated margins.

The accompanying illustration shows the bloom and a spray of matured leaves, and a single flower in its fully matured coloring.

The color characteristics of my new variety according to Maerz and Paul Dictionary of Color are shown in the following table:

| Item | Plate | Ltr. | No. |
|---|---|---|---|
| Open flowers (new) | 1 | A | 1 |
| Tipped with | 1 | C | 2 |
| Open flowers (old) | 1 | C | 2 |
| Stamens tipped with | 9 | L | 5 |
| Buds | 10 | E | 1 |
| Tipped with | 41 | E | 2 |
| Calyx | 17 | J | 7 |
| Leaves | 22 | L | 8 |
| Stems | 7 | A | 10 |

The common variety of *Chaenomeles lagenaria*, Koidzumi, is a shrub of three to six feet with spreading spiny branches and flowers of a solid color. Its leaves are ovate or oblong in shape.

The hereindescribed plant is particularly characterized by the prolific quantity and size of the blooms; the unique coloring at its different stages of development contrasting most pleasingly with the yellow color of the anthers; the shape and coloring of its green leaves; and its particularly good lasting quality as a cut flower.

Having thus disclosed my invention, I claim:

A new and distinct variety of plant of the species *Chaenomeles lagenaria,* Koidzumi, substantially as described, being characterized by the changing and distinctive colors of its blooms, appearing during different stages of development, being pure white at first, then tinged with pink tips and finally turning to a soft rose; the habit of its first blooms being single-petaled and the later ones double-petaled; the shape and coloring of its leaves, and its superior keeping quality as a cut flower.

WALTER BOSWORTH CLARKE.

No references cited.